(12) United States Patent
Fan et al.

(10) Patent No.: US 12,343,123 B2
(45) Date of Patent: Jul. 1, 2025

(54) HEART RHYTHM DETECTION CONTROL METHOD AND TERMINAL

(71) Applicant: HUAWEI TECHNOLOGIES CO., LTD., Guangdong (CN)

(72) Inventors: Jingwen Fan, Shanghai (CN); Huangwei Wu, Shenzhen (CN); Jie Zhang, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 337 days.

(21) Appl. No.: 17/995,101

(22) PCT Filed: Mar. 17, 2021

(86) PCT No.: PCT/CN2021/081244
§ 371 (c)(1),
(2) Date: Sep. 29, 2022

(87) PCT Pub. No.: WO2021/203930
PCT Pub. Date: Oct. 14, 2021

(65) Prior Publication Data
US 2023/0172464 A1 Jun. 8, 2023

(30) Foreign Application Priority Data
Apr. 8, 2020 (CN) .................. 202010269301.X (51) Int. Cl.
*A61B 5/024* (2006.01)
*A61B 5/00* (2006.01)
*A61B 5/11* (2006.01)
*G06F 3/0488* (2022.01)

(52) U.S. Cl.
CPC ........ *A61B 5/02416* (2013.01); *A61B 5/1112* (2013.01); *A61B 5/72* (2013.01); *G06F 3/0488* (2013.01)

(58) Field of Classification Search
CPC ........................ A61B 5/02416; A61B 5/1112
USPC ........................................................ 600/301
See application file for complete search history.

(56) References Cited

U.S. PATENT DOCUMENTS

| 6,650,940 | B1 | 11/2003 | Zhu et al. |
| 7,285,090 | B2 * | 10/2007 | Stivoric ............... A61B 5/7264 |
| | | | 128/920 |
| 10,213,162 | B2 | 2/2019 | Fung et al. |
| 10,278,647 | B2 | 5/2019 | Salehizadeh et al. |

(Continued)

FOREIGN PATENT DOCUMENTS

| CN | 1894975 A | 1/2007 |
| CN | 100456804 C | 1/2009 |
| CN | 101636783 A | 1/2010 |

(Continued)

*Primary Examiner* — Nadia A Mahmood (57) ABSTRACT

A heart rhythm detection control method and a terminal relate to the field of terminal technologies, and can reduce, to some extent, an inaccurate heart rhythm detection result displayed by a terminal. The heart rhythm detection control method includes: detecting motion data of the terminal in response to a heart rhythm detection instruction input by a user; and if the motion data is greater than a motion data threshold, displaying first prompt information in a user interface. The first prompt information is used to prompt the user that heart rhythm detection is suspended.

20 Claims, 7 Drawing Sheets

(56) References Cited

U.S. PATENT DOCUMENTS

2012/0283544 A1    11/2012    Kraetschmer et al.

FOREIGN PATENT DOCUMENTS

| CN | 1993707 | B | 12/2012 |
|----|---------|---|---------|
| CN | 202794796 | U | 3/2013 |
| CN | 101617339 | B | 7/2013 |
| CN | 103379196 | A | 10/2013 |
| CN | 103456301 | A | 12/2013 |
| CN | 103986866 | A | 8/2014 |
| CN | 104083152 | A | 10/2014 |
| CN | 104320577 | A | 1/2015 |
| CN | 105049569 | A | 11/2015 |
| CN | 105391866 | A | 3/2016 |
| CN | 105796091 | A | 7/2016 |
| CN | 105919584 | A | 9/2016 |
| CN | 205579323 | U | 9/2016 |
| CN | 206021231 | U | 3/2017 |
| CN | 106691423 | A | 5/2017 |
| CN | 107405087 | A | 11/2017 |
| CN | 107536599 | A | 1/2018 |
| CN | 107582036 | A | 1/2018 |
| CN | 104902177 | B | 3/2018 |
| CN | 107846547 | A | 3/2018 |
| CN | 104580910 | B | 7/2018 |
| CN | 108392193 | A | 8/2018 |
| CN | 106056601 | B | 10/2018 |
| CN | 109875543 | A | 6/2019 |
| CN | 110022762 | A | 7/2019 |
| JP | 2015058022 | A | 3/2015 |

\* cited by examiner

HEART RHYTHM DETECTION CONTROL METHOD AND TERMINAL

CROSS-REFERENCE TO RELATED APPLICATIONS

This application is a National Stage of International Application No. PCT/CN2021/081244, filed on Mar. 17, 2021, which claims priority to Chinese Patent Application No. 202010269301.X, filed on Apr. 8, 2020, both of which are hereby incorporated by reference in their entireties.

TECHNICAL FIELD

This application relates to the field of terminal technologies, and in particular, to a heart rhythm detection control method and a terminal.

BACKGROUND

At present, a smart watch usually has a function of detecting the heart rhythm of a user through photoplethysmography (Photo Plethysmo Graphy, PPG). When the user has arrhythmia, the smart watch issues an alarm to prompt the user.

The user needs to keep relatively quiet and still in a process of detecting the heart rhythm by the smart watch, so that the detection can succeed or a relatively accurate detection result can be obtained. However, in some scenarios, for example, when the user is in a vehicle, although the user keeps still relative to the moving vehicle, a PPG signal is greatly interfered with due to the motion of the vehicle, resulting in an inaccurate heart rhythm detection result of the smart watch.

SUMMARY

This application provides a heart rhythm detection control method and a terminal, to resolve a problem that heart rhythm detection data of a terminal is inaccurate in a motion scenario in the conventional technology.

To achieve the foregoing objective, the following technical solutions are used in this application.

According to a first aspect, an embodiment provides a heart rhythm detection control method, applied to a terminal. The method includes: detecting motion data of the terminal in response to a heart rhythm detection instruction input by a user; and if the motion data is greater than a motion data threshold, displaying first prompt information in a user interface. The first prompt information is used to prompt the user that heart rhythm detection is suspended.

According to the heart rhythm detection control method provided in this embodiment, the current heart rhythm detection can be suspended, and the first prompt information is displayed, to guide the user to give up the current heart rhythm detection. Therefore, a possibility that the terminal obtains an inaccurate heart rhythm detection result is reduced to some extent.

With reference to the first aspect, in some embodiments, a confirm icon and an exit icon are further displayed in the user interface. The confirm icon is used to control the terminal to perform heart rhythm detection in response to a confirm operation input by the user. The exit icon is used to control the terminal to exit the user interface in response to an exit operation input by the user. By using the displayed interface, the user can independently choose whether to perform detection at the risk of an inaccurate detection result, which helps improve user experience.

With reference to the first aspect, in some embodiments, when an automatic detection mode is enabled on the terminal, the method further includes: detecting motion data of the terminal; and when detecting that the motion data is greater than the motion data threshold, suspending the automatic detection mode; or when detecting that the motion data is less than or equal to the motion data threshold, enabling the automatic detection mode.

When the motion data of the terminal is greater than the motion data threshold, it indicates that the terminal is in a bumping state, and it is very difficult for the terminal to accurately detect a heart rhythm, especially detect premature heartbeats and atrial fibrillation. A detection result often cannot be obtained even after continuous PPG data collection and analysis. Therefore, when the motion data of the terminal is greater than the motion data threshold, the automatic detection of the user's heart rhythm is suspended, to avoid an invalid and inaccurate heart rhythm detection result.

With reference to the first aspect, in some embodiments, when detecting that the motion data is greater than the motion data threshold, the method further includes: displaying second prompt information in the user interface. The second prompt information is used to prompt the user that the automatic detection mode is suspended. When detecting that the motion data changes from being greater than the motion data threshold to being less than or equal to the motion data threshold, the method further includes: displaying third prompt information in the user interface. The third prompt information is used to prompt the user that the automatic detection mode is enabled.

The user can be notified of a progress of automatic heart rhythm detection by displaying the second prompt information and the third prompt information, which helps improve user experience.

With reference to the first aspect, in some embodiments, the motion data includes a speed and/or acceleration.

With reference to the first aspect, in some embodiments, when the motion data is greater than the motion data threshold, the method further includes: recognizing ambient sound information of an environment in which the terminal is located; and if the ambient sound information includes preset vehicle characteristic information, displaying vehicle prompt information in the user interface, where the vehicle prompt information is used to prompt the user that the terminal is currently in a running vehicle.

When the motion data of the terminal is greater than the motion data threshold, the terminal is in a bumping state. In this case, by recognizing the ambient sound information of the terminal, it can be further determined whether the current bumping state is caused by running of the vehicle, so that the terminal informs, by using the prompt information, the user of a cause for suspending the heart rhythm detection. For example, the terminal may display "The vehicle is running. Please perform detection after the vehicle is parked". Alternatively, the terminal may display "The vehicle is running, and automatic heart rhythm detection is suspended".

According to a second aspect, an embodiment provides a heart rhythm detection control apparatus, applied to a terminal. The apparatus includes: a detection module, configured to detect motion data of the terminal in response to a heart rhythm detection instruction input by a user; and a control module, configured to: if the motion data is greater than a motion data threshold, display first prompt information in a user interface, where the first prompt information is used to prompt the user that heart rhythm detection is suspended.

According to a third aspect, an embodiment provides a terminal, including a heart rhythm detection module, a display module, a memory, a processor, and a computer program stored on the memory and executable on the processor. The processor executes the computer program to implement the method according to the first aspect.

According to a fourth aspect, an embodiment provides a computer-readable storage medium having a computer program stored thereon. When the computer program is executed by a processor, the method according to the first aspect is implemented.

According to a fifth aspect, an embodiment provides a computer program product including a program. The program, when run by a terminal device, causes the terminal device to implement the method according to any one of the first aspect or the possible implementations of the first aspect.

It may be understood that for beneficial effects of the second aspect to the fifth aspect, refer to the related description in the first aspect, and details are not described herein again.

DETAILED DESCRIPTION OF EMBODIMENTS

A heart rhythm detection control method provided in the embodiments can be applied to a terminal having a heart rhythm detection function, such as a smart watch, a fitness band, or smart jewelry. The embodiments of this application do not impose any limitation on a specific type of the terminal.

It should be understood that the first, the second, and various numbers in this specification are used for differentiation only for ease of description, instead of limiting the scope of this application.

It should also be understood that the term "and/or" in this specification describes only an association relationship for describing associated objects and represents that three relationships may exist. For example, A and/or B may represent the following three cases: Only A exists, both A and B exist, and only B exists. In addition, the character "/" in this specification generally indicates an "or" relationship between the associated objects.

Figure 1:
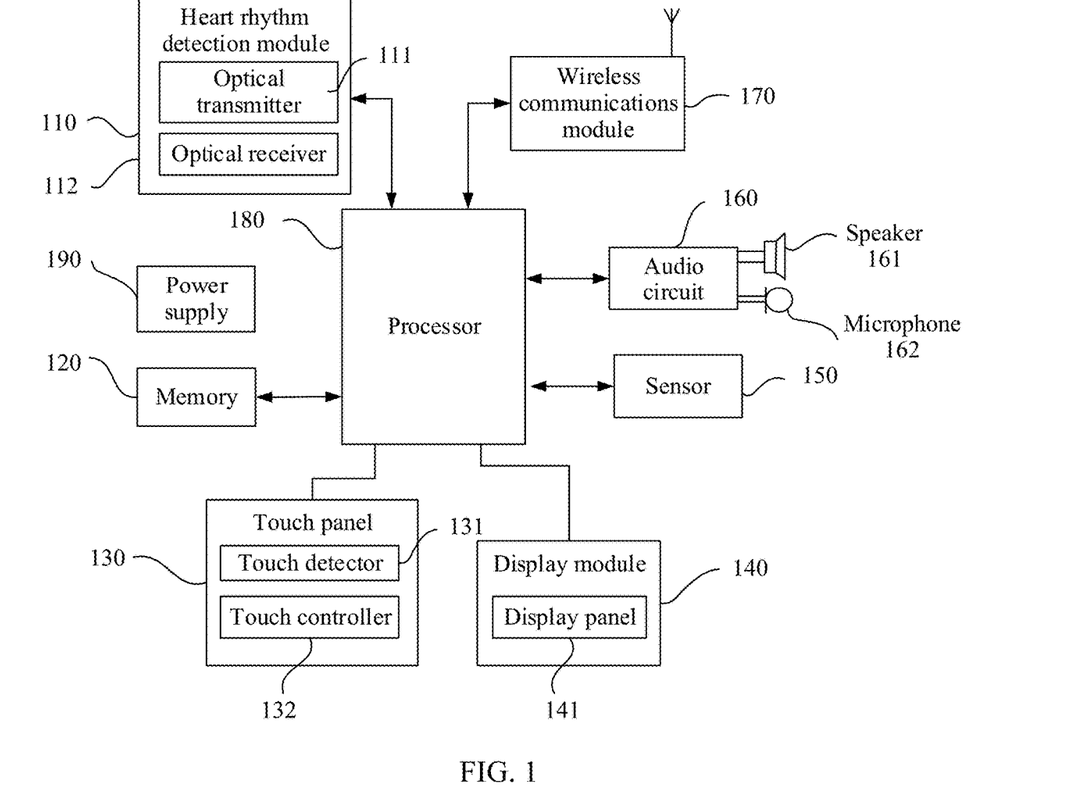
FIG. 1 is a diagram of a system architecture of a terminal according to an embodiment of this application.

FIG. 1 is a block diagram of a partial structure of a terminal according to an embodiment. Refer to FIG. 1. The terminal includes components such as a heart rhythm detection module 110, a memory 120, a touch panel 130, a display module 140, a sensor 150, an audio circuit 160, a wireless communications module 170, and a processor 180. A person skilled in the art may understand that the terminal structure shown in FIG. 1 does not constitute a limitation to the terminal. The terminal may include more or fewer components than those shown in the figure, or some components may be combined, or there may be a different component arrangement.

The heart rhythm detection module 110 is configured to detect a heart rhythm of a user based on a PPG technology, where the heart rhythm includes, but is not limited to, a frequency of heartbeats (that is, a heart rate), premature heartbeats, atrial fibrillation, and the like. The heart rhythm detection module 110 includes an optical transmitter 111 and an optical receiver 112. The optical transmitter 111 is configured to transmit an optical signal of a specific wavelength, for example, 800 nm to 960 nm. The optical receiver 112 is configured to receive and convert a returned optical signal into an electrical signal, then convert the electrical signal into a digital signal, and finally send the digital signal to the processor 180. The processor 180 performs heart rhythm detection by using a predetermined heart rhythm screening model.

When the optical signal from the optical transmitter 111 strikes the human skin tissue and then is reflected to the optical receiver 112, a light intensity is attenuated to some extent. This is because an amount of light absorbed by muscles, bones, veins, and other connecting tissues remains basically unchanged when a human body does not move substantially. However, this is the other case for an artery. A blood volume in the artery varies periodically depending on contraction and relaxation of the heart. When the heart contracts, the blood volume in the artery increases, an amount of light absorbed increases, and an intensity of reflected light decreases. When the heart relaxes, the blood volume in the artery decreases, an amount of light absorbed decreases, and an intensity of reflected light increases. When light strikes a part where the artery is located (for example, the inner side of a wrist), a total amount of light absorbed changes periodically, and an intensity of the reflected light received by the optical receiver 112 changes periodically. Based on the law of changes in the intensity of the reflected light, the law of changes in the pulse can be determined, and then the heart rhythm of the human body can be determined.

The memory 120 may be configured to store software programs and modules, and the processor 180 executes various functional applications and data processing of the terminal by running the software programs and the modules stored on the memory 120. The memory 120 may mainly include a program storage area and a data storage area. The program storage area may store an operating system, an application program required by at least one function (for example, an image display function and a heart rhythm detection function), and the like. The data storage area may store data (for example, heart rhythm data and motion data) and the like created according to the use of the terminal. In addition, the memory 120 may include a high-speed random access memory, or may include a nonvolatile memory, such as at least one magnetic disk storage device, a flash memory device, or another volatile solid-state storage device.

The touch panel 130, also referred to as a touchscreen, may capture a touch operation performed by a user on or near the touch panel 130 (for example, an operation performed by a user on the touch panel 130 or near the touch panel 130 by using any appropriate object or accessory such as a finger or a stylus), and drive a corresponding connection apparatus based on a preset program. Optionally, the touch panel 130 may include two parts: a touch detector 131 and a touch controller 132. The touch detector 131 detects a touch position of the user and detects a signal resulting from the touch operation, and transmits the signal to the touch controller 132. The touch controller 132 receives and converts the touch information from the touch detector 131 into touch point coordinates, and then sends the touch point coordinates to the processor 180. In addition, the touch controller can receive and execute a command sent by the processor 180. In addition, the touch panel 130 may be implemented by using a plurality of types, such as a resistive type, a capacitive type, an infrared ray type, and a surface acoustic wave type.

The display module 140 may be configured to display information input by the user or information provided for the user and various menus of the terminal. The display module 140 may include a display panel 141. Optionally, the display panel 141 may be configured in a form of liquid crystal display (Liquid Crystal Display, LCD), organic light-emitting diode (Organic Light-Emitting Diode, OLED), or the like. Further, the touch panel 130 may cover the display panel 141. When detecting a touch operation on or near the touch panel 130, the touch panel 130 transmits the touch operation to the processor 180 to determine a type of a touch event. Then the processor 180 provides corresponding visual output on the display panel 141 based on the type of the touch event. In FIG. 1, the touch panel 130 and the display panel 141 are used as two independent components to implement input and output functions of the terminal. However, in some embodiments, the touch panel 130 and the display panel 141 may be integrated to implement the input and output functions of the terminal.

The terminal may further include at least one sensor 150, for example, a light sensor, a motion sensor, and another sensor. Specifically, the light sensor may include an ambient light sensor and a proximity sensor, where the ambient light sensor can adjust brightness of the display panel 141 based on luminance of ambient light, and the proximity sensor can turn off the display panel 141 and/or backlight when the terminal moves towards an ear. As a type of motion sensor, an acceleration sensor can detect magnitudes of accelerations in all directions (usually three axes), and can be applied to functions related to vibration recognition (such as a pedometer and tapping), and the like.

The audio circuit 160, a speaker 161, and a microphone 162 can provide an audio interface between the user and the terminal. The audio circuit 160 can transmit an electrical signal converted from received audio data to the speaker 161, and the speaker 161 converts the electrical signal into a sound signal and outputs the sound signal. In addition, the microphone 162 converts the collected sound signal into an electrical signal, which is then received by the audio circuit 160 and converted into audio data. After being output to the processor 180 for processing, the audio data is output to the memory 120 for further processing.

The wireless communications module includes wireless fidelity (Wireless Fidelity, Wi-Fi) and Bluetooth. Both Wi-Fi and Bluetooth are short-range wireless transmission technologies to help users send and receive information. Although FIG. 1 shows the wireless communications module 180, it may be understood that the wireless communications module is not a necessary component of the terminal, and can be completely omitted without changing the essence of the invention as required.

The processor 180 is a control center of the terminal, and connects all parts of the entire terminal by using various interfaces and lines. By running or executing a software program and/or a module stored in the memory 120 and invoking data stored in the memory 120, the processor 180 performs various functions of the terminal and data processing, so as to perform overall monitoring on the terminal. Optionally, the processor 180 may include one or more processing units. Preferably, the processor 180 may integrate an application processor and a modem processor. The application processor mainly processes an operating system, a user interface, an application, and the like. The modem processor mainly processes wireless communication. It may be understood that the foregoing modem processor may be not integrated into the processor 180.

The terminal further includes a power supply 190 (for example, a battery) that supplies power to various components. Preferably, the power supply may be logically connected to the processor 180 through a power supply management system, so that functions such as charging and discharging management and power consumption management are implemented by using the power management system.

The terminal provided in this embodiment may include two heart rhythm detection modes: an active detection mode and an automatic detection mode.

In the active detection mode, the terminal performs one heart rhythm detection operation every time a heart rhythm detection instruction input by the user is received. The active detection mode is usually enabled automatically after the terminal is powered on, and can work simultaneously with the automatic detection mode. In other words, when the automatic detection mode is enabled, the terminal can also detect the heart rhythm based on the user's active operation.

In the automatic detection mode, the terminal detects the user's heart rhythm every preset time (for example, every 10 minutes), and stores a detection result for later review and analysis by the user. In this embodiment, the user can choose whether to enable the automatic detection mode of the terminal according to the user's needs. Certainly, in some other embodiments, the automatic detection mode of the terminal may alternatively be enabled all the time, and cannot be disabled by the user.

When the user uses the terminal, for example, when the user walks, runs, swims, or rides a vehicle, the terminal moves along. However, when the terminal moves substantially and is in a bumping state, it may cause the terminal to obtain an inaccurate heart rhythm detection result, or even cause the heart rhythm detection to fail. Therefore, this application provides a heart rhythm detection control method, which can prevent, to some extent, a terminal from obtaining an inaccurate heart rhythm detection result in a bumping state.

The following provides example descriptions of heart rhythm detection control methods respectively in an active detection mode and an automatic detection mode provided in the embodiments.

Figure 2:
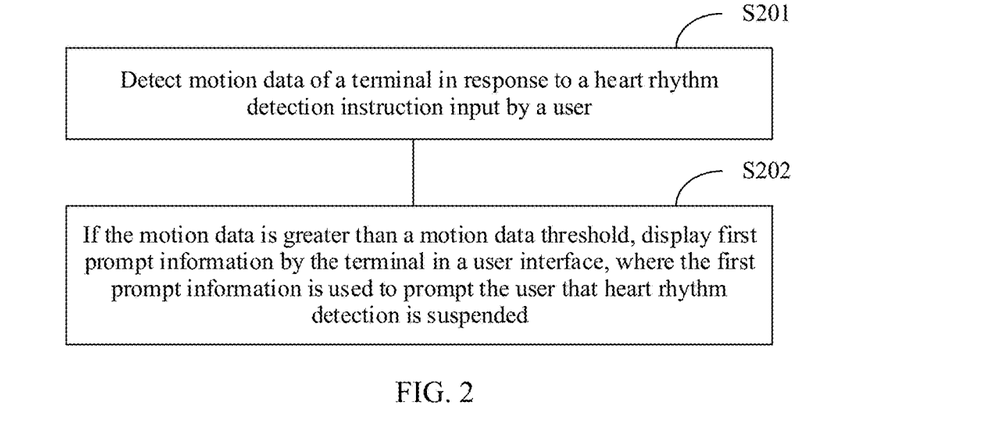
FIG. 2 is a schematic flowchart 1 of a heart rhythm detection control method according to an embodiment of this application.

FIG. 2 is a flowchart of a heart rhythm detection control method according to an embodiment, and mainly describes a heart rhythm detection control method in an active detection mode. As shown in FIG. 2, the method includes step S201 and step S202.

S201: Detect motion data of a terminal in response to a heart rhythm detection instruction input by a user.

Figure 3:
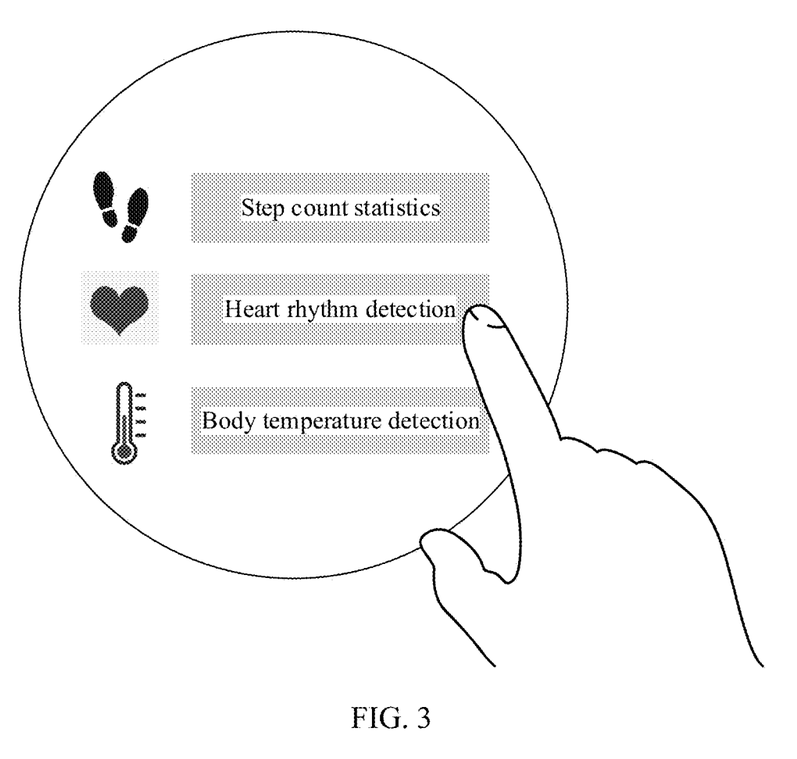
FIG. 3 is a schematic diagram 1 of a user interface of a terminal according to an embodiment of this application.

When the user wants to perform heart rhythm detection, the user may tap a heart rhythm detection icon in a user interface of the terminal to input a heart rhythm detection instruction. For example, as shown in FIG. 3, the user interface may include a step count statistics icon, a heart rhythm detection icon, and a body temperature detection icon. After detecting that the user taps the heart rhythm detection icon, the terminal determines that the heart rhythm detection instruction input by the user is received. The terminal detects its own motion data in response to the heart rhythm detection instruction.

In this embodiment, the motion data may include a speed and/or acceleration. A motion state of the terminal may be determined based on the motion data. For example, it can be determined whether the terminal is in a bumping state or a stable state.

S202: If the motion data is greater than a motion data threshold, the terminal displays first prompt information in the user interface, where the first prompt information is used to prompt the user that heart rhythm detection is suspended.

The terminal may detect the acceleration by using a built-in acceleration sensor. Alternatively, the speed and acceleration may be detected by using a global positioning system (Global Positioning System, GPS) speed measurement technology.

In this embodiment, the motion data being greater than the motion data threshold includes the speed being greater than a speed threshold, and/or the acceleration being greater than an acceleration threshold. When detecting that the motion data is greater than the motion data threshold, it is determined that the terminal is in a bumping state.

The motion data being less than or equal to the motion data threshold includes the speed being less than or equal to the speed threshold, and/or the acceleration being less than or equal to the acceleration threshold. When detecting that the motion data is less than or equal to the motion data threshold, it is determined that the terminal is in a stable state.

In this embodiment, the speed threshold and the acceleration threshold are preconfigured. For example, the speed threshold may be 5 meters/second (m/s), 10 m/s, 15 m/s, or the like, and the acceleration threshold may be 2 meters/second squared (m/s2), 5 m/s2, 10 m/s2, or the like, which is not limited in this embodiment.

Figure 4:
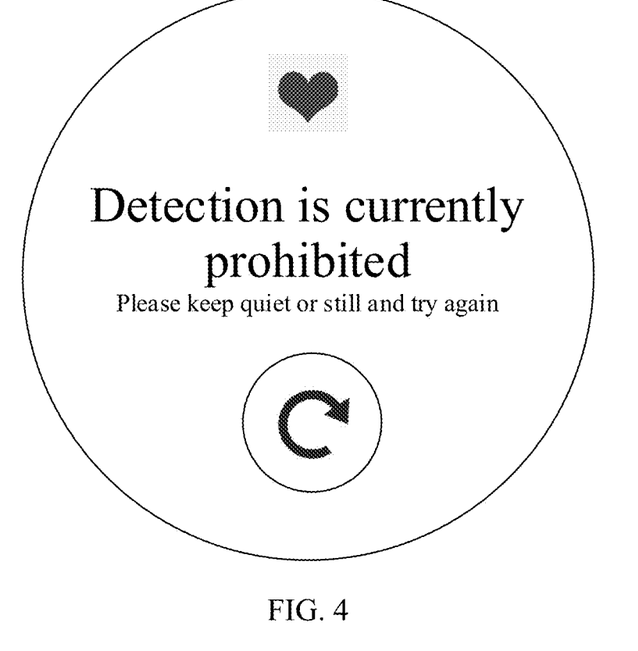
FIG. 4 is a schematic diagram 2 of a user interface of a terminal according to an embodiment of this application.

In a possible implementation, if the motion data is greater than the motion data threshold, the terminal is configured to prohibit heart rhythm detection. In this case, the first prompt information is used to prompt the user that heart rhythm detection is currently prohibited. For example, as shown in FIG. 4, the terminal may display the first prompt information: "Detection is currently prohibited. Please keep quiet or still and try again" in the user interface. In addition, a retry icon is displayed in the user interface for the user to re-input the heart rhythm detection instruction.

When the motion data of the terminal is greater than the motion data threshold, the terminal is in a bumping state, and the result of heart rhythm detection may be inaccurate or a detection failure may occur. Therefore, in this embodiment, when detecting that the motion data is greater than the motion data threshold, the heart rhythm detection is suspended and prohibited. This can prevent the terminal from obtaining an inaccurate heart rhythm detection result, and can also avoid a detection failure generated when the terminal cannot obtain a heart rhythm detection result after collecting PPG data with great interference.

In addition, compared with the fact that the terminal can determine a detection failure and display failure prompt information only after PPG data collection and analysis, in this embodiment, the first prompt information is displayed once it is detected that the motion data of the terminal is greater than the motion data threshold, which can prevent the user from experiencing a futile detection wait, improving user experience.

Figure 5:
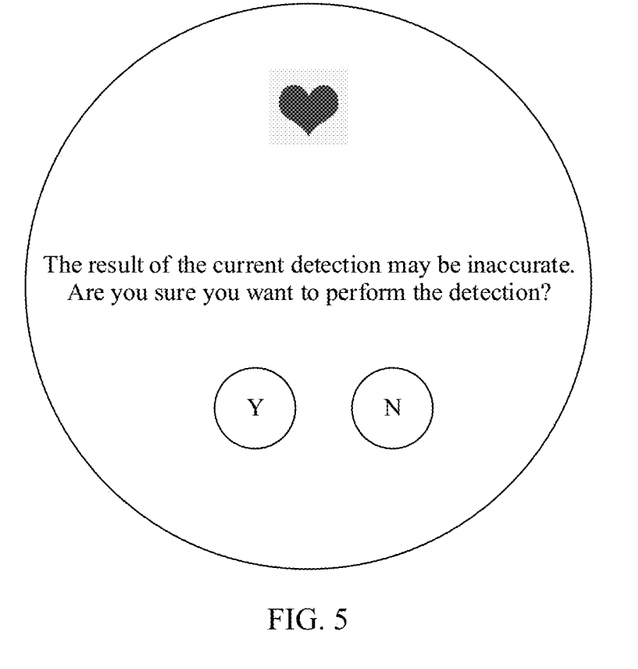
FIG. 5 is a schematic diagram 3 of a user interface of a terminal according to an embodiment of this application.

In another possible implementation, the terminal is configured to: when the motion data is greater than the motion data threshold, use the first prompt information to inform the user of the risk of the current detection, and then determine whether to perform the detection according to an instruction of the user. For example, as shown in FIG. 5, the terminal may display the first prompt information: "The result of the current detection may be inaccurate. Are you sure you want to perform the detection?" in the user interface. At the same time, a confirm icon (such as a Y icon) and an exit icon (such as an Nicon) are displayed in the user interface. The user taps the confirm icon to start the current heart rhythm detection; or the user may tap the exit icon to exit the current user interface and cancel the detection.

It should be noted that the user can be guided to give up the current detection by using the first prompt information to inform the user of the risk of the current heart rhythm detection in advance, which prevents, to some extent, the terminal from obtaining an inaccurate heart rhythm detection result in a bumping state. In addition, a quantity of heart rhythm detections of the terminal in a bumping scenario can be reduced, thereby increasing a total success rate of the heart rhythm detections of the terminal.

Moreover, the first prompt information may further lower the user's expectations of the result of the current detection, making it easier for the user to accept an inaccurate result of the current heart rhythm detection or a detection failure, which helps improve user experience.

Figure 6:
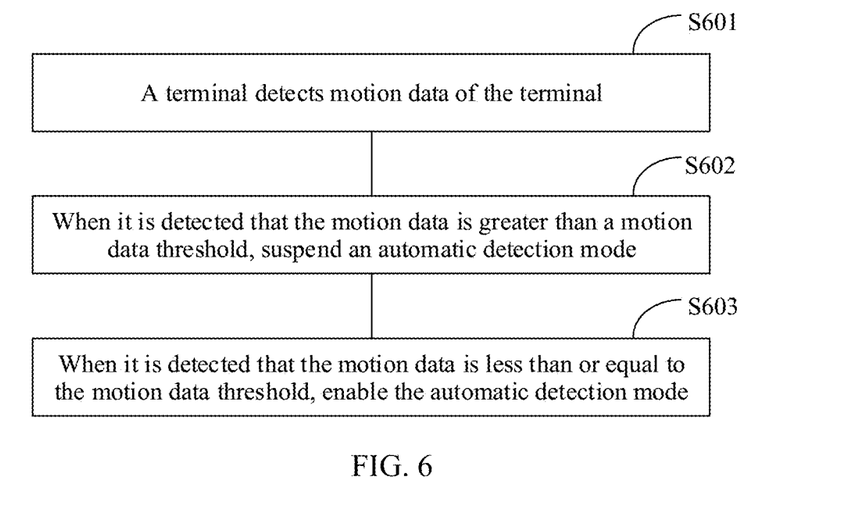
FIG. 6 is a schematic flowchart 2 of a heart rhythm detection control method according to an embodiment of this application.

FIG. 6 is a flowchart of another heart rhythm detection control method according to an embodiment, and mainly describes a heart rhythm detection control method in an automatic detection mode. As shown in FIG. 6, the method includes step S601 to step S603.

S601: A terminal automatically detects motion data of the terminal.

In the automatic detection mode, the terminal may detect motion data once before each heart rhythm detection. Alternatively, motion data is detected once every preset time. The preset time is less than or equal to a time interval for automatically detecting the heart rhythm, and may be 10 seconds, 30 seconds, 5 minutes, or the like. In addition, in step S601, for the detection process of the motion data, refer to the description of step S201, and details are not described here again in this embodiment.

S602: When the terminal detects that the motion data is greater than a motion data threshold, suspend the automatic detection mode.

In the automatic detection mode, the terminal can automatically detect the user's heart rhythm, and store a detection result for later analysis and review by the user to know about the health status. Therefore, when the motion data is greater than the motion data threshold, the terminal is in a bumping state, and the automatic detection of the user's heart rhythm may be suspended to avoid an invalid and inaccurate heart rhythm detection result.

Figure 7:
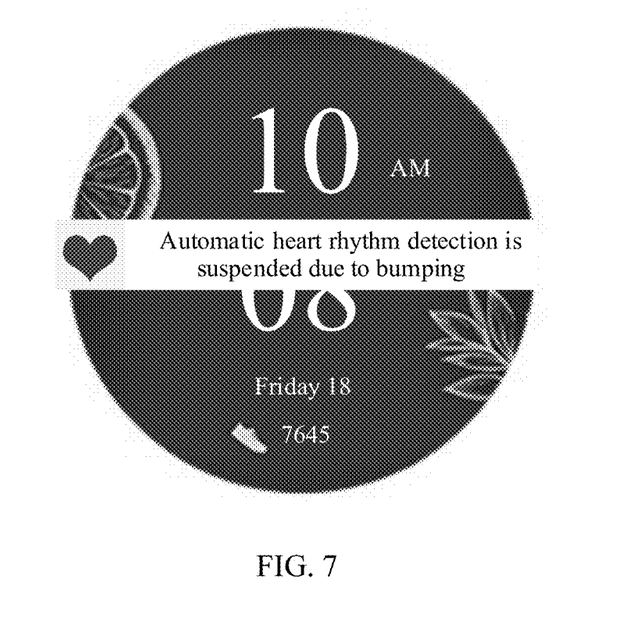
FIG. 7 is a schematic diagram 4 of a user interface of a terminal according to an embodiment of this application.

In an optional implementation, after suspending the automatic heart rhythm detection, the terminal displays second prompt information to prompt the user that the automatic heart rhythm detection is suspended. For example, in a display interface shown in FIG. 7, the terminal displays the second prompt information: "Automatic heart rhythm detection is suspended due to bumping".

S603: When the terminal detects that the motion data is less than or equal to the motion data threshold, enable the automatic detection mode.

Figure 8:
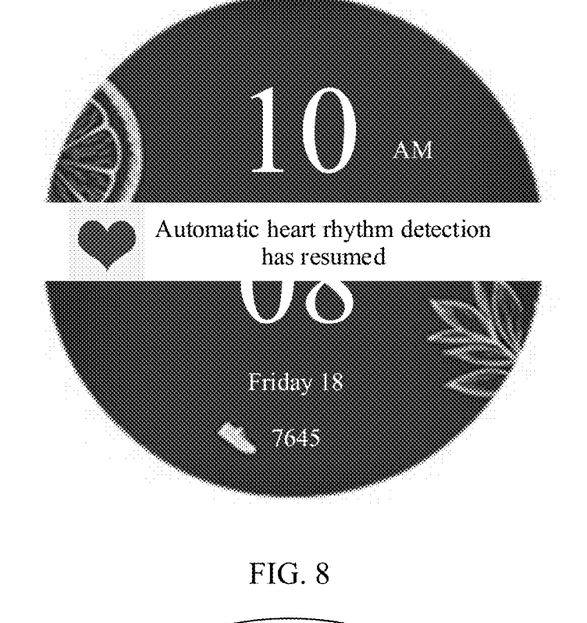
FIG. 8 is a schematic diagram 5 of a user interface of a terminal according to an embodiment of this application.

In an optional implementation, when the terminal detects the motion data, if it is detected that the motion data of the terminal changes from being greater than the motion data threshold to being less than or equal to the motion data threshold, that is, the result of the current detection is less than or equal to the motion data threshold, but the result of the last detection is greater than the motion data threshold, the terminal displays third prompt information in the user interface. In this case, a motion terminal of the terminal changes from a bumping state to a stable state, and the third prompt information is used to prompt the user that the automatic heart rhythm detection is started. For example, in a display interface shown in FIG. 8, the terminal displays the third prompt information: "Automatic heart rhythm detection has resumed".

In addition, when the motion data is greater than the motion data threshold, and the terminal is in a bumping state, to further determine whether the current bumping state is caused by riding a vehicle, the terminal may recognize ambient sound information of an environment in which the terminal is located. If the ambient sound information includes vehicle characteristic information, such as navigation sound from the vehicle, sound of a turn signal, announcement sound from a bus and subway, or sound of opening and closing doors, it indicates that the terminal is in the vehicle, and the current bumping state is caused by the motion of the vehicle.

It should be noted that, by determining whether the current bumping state is caused by riding a vehicle, the terminal can give a control operation and a detection suggestion for the user's riding scenario in the subsequent heart rhythm detection control process, which helps increase heart rhythm detection accuracy and improve user experience. For example, the terminal may use the first prompt information or the second prompt information to inform the user of a motion scenario of the terminal.

Figure 9:
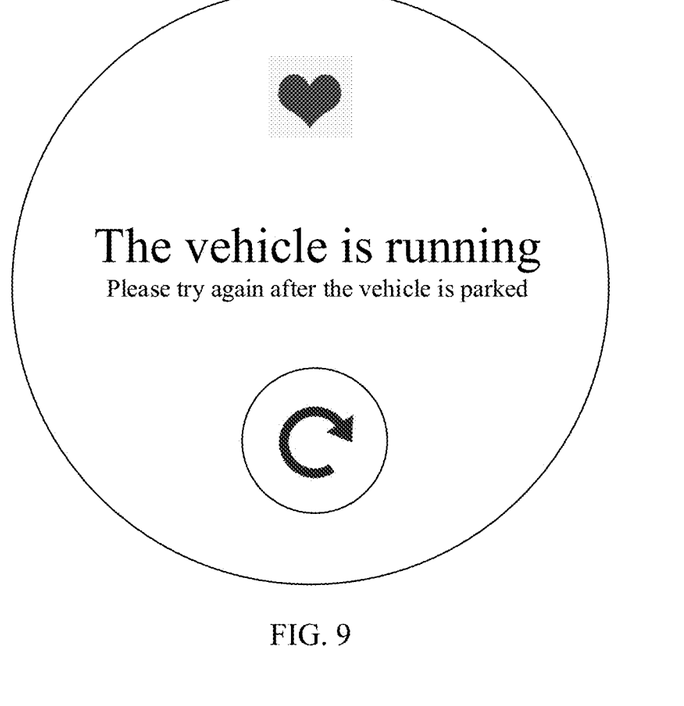
FIG. 9 is a schematic diagram 6 of a user interface of a terminal according to an embodiment of this application.

Refer to FIG. 9. The terminal may display the first prompt information "The vehicle is running. Please perform detection after the vehicle is parked". Informing the user of the motion scenario of the terminal enables the user to directly know about a cause for which the current detection is not allowed, which prevents the user from continuing to make futile attempts in the running state of the vehicle.

Figure 10:
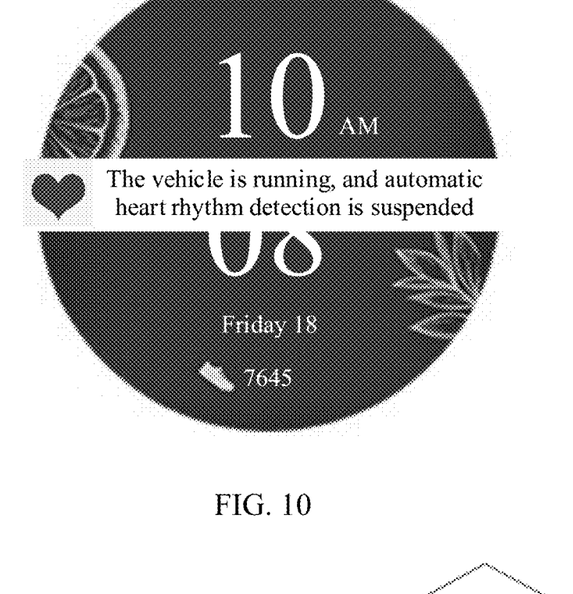
FIG. 10 is a schematic diagram 7 of a user interface of a terminal according to an embodiment of this application.

Refer to FIG. 10. The terminal may display the second prompt information "The vehicle is running, and automatic heart rhythm detection is suspended", so that the user can know about the direct cause for which the automatic heart rhythm detection is suspended.

Figure 11:
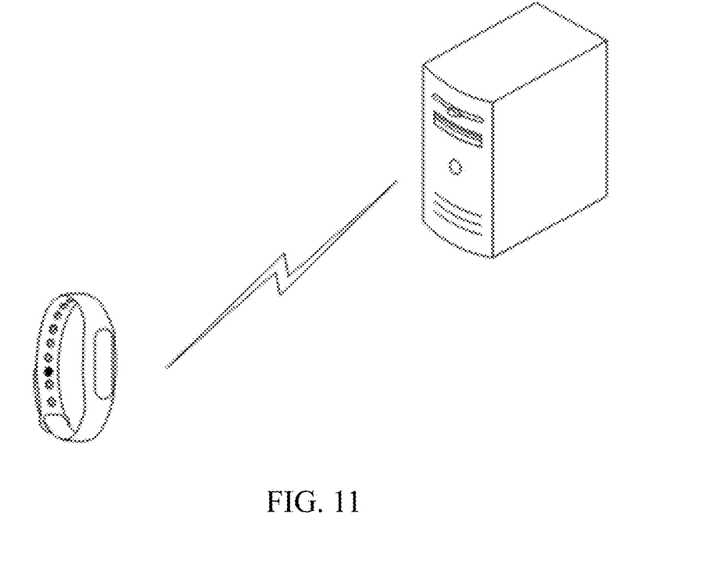
FIG. 11 is a schematic diagram of a structure of a connection between a terminal and a server according to an embodiment of this application.

In this embodiment, refer to FIG. 11, and the terminal may recognize ambient sound information by using a server having a sound recognition function. The server may be a self-operated server or a third-party server. In the process of recognizing the ambient sound information, the terminal sends the collected ambient sound information to the server. After receiving the ambient sound information, the server compares the ambient sound information with a local vehicle characteristic information repository. The vehicle characteristic information repository pre-stores characteristic sounds of various vehicles, including but not limited to, the preceding navigation sound from the vehicle, sound of a turn signal, announcement sound from a public transport, sound of opening and closing doors, or the like. If the ambient sound information includes any piece of sound information in the vehicle characteristic information repository, it is determined that the terminal is in the vehicle. After completing the recognition of the sound signal, the server sends a recognition result to the terminal.

Figure 12:
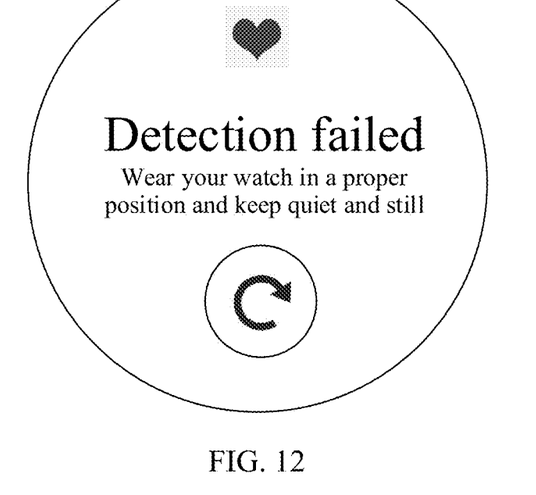
FIG. 12 is a schematic diagram 8 of a user interface of a terminal according to an embodiment of this application.

In addition, in this embodiment, in the heart rhythm detection process of the terminal, the light intensity between the skin and the terminal may be detected by using a light sensor disposed on the back of the terminal (i.e., on the side close to the skin). If the light intensity is higher than a preset intensity, it indicates that the terminal does not fit closely with the skin, and the user does not wear the terminal correctly. In this case, the heart rhythm detection stops, and the terminal displays a detection failure interface. For example, the detection failure interface may be shown in FIG. 12, displaying failure prompt information: "Detection failed. Please wear your watch in a proper position and keep quiet and still."

In addition, in a bumping state caused by the motion of the vehicle, when the terminal detects the user's heart rhythm based on a PPG signal, an artifact removal technology may be used first to remove a part of the interference in the PPG signal caused by bumping. The quality of the PPG signal after the disturbance is removed may be degraded. Therefore, the terminal may lower a quality checking criterion for the PPG signal to avoid losing too many PPG signals. Then an onboard heart rhythm screening model is used to detect the user's heart rhythm based on the disturbance-removed PPG signal. It should be noted that the onboard heart rhythm screening model is obtained by training in advance based on the onboard PPG data after the disturbance is removed. For the specific training process, refer to the conventional technology, which is not described here in detail in this embodiment.

Removing the disturbance in the PPG signal and using the onboard heart rhythm screening model to detect the heart rhythm can increase the accuracy of the heart rhythm detection during the onboard process and improve user experience.

Figure 13:
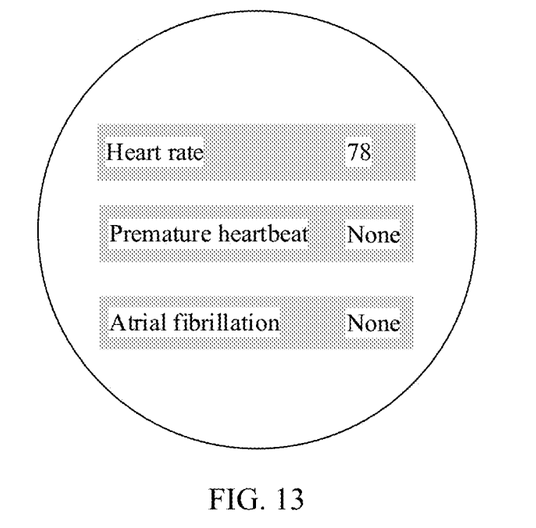
FIG. 13 is a schematic diagram 9 of a user interface of a terminal according to an embodiment of this application.

After the terminal completes the heart rhythm detection, the detection result is displayed in the user interface. The detection result may include a heart rate value, a condition of premature heartbeats, and a condition of atrial fibrillation of the user. For example, the user interface may be shown in FIG. 13, and the displayed heart rhythm detection result is: a heart rate of 78, no premature heartbeats, and no atrial fibrillation.

It should be understood that sequence numbers of the steps do not mean an execution sequence in the foregoing embodiments. The execution sequence of the processes should be determined based on functions and internal logic of the processes, and should not constitute any limitation on the implementation processes of embodiments of this application.

Figure 14:
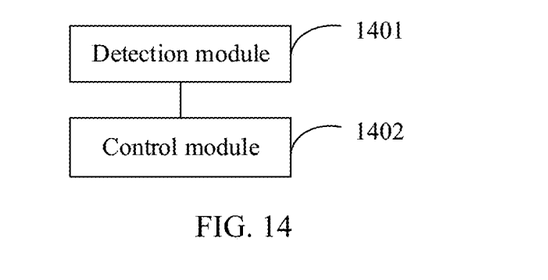
FIG. 14 is a schematic diagram of a structure of a heart rhythm detection control apparatus according to an embodiment of this application.

Corresponding to the heart rhythm detection control method described in the foregoing embodiment, FIG. 14 is a block diagram of a structure of a heart rhythm detection control apparatus according to an embodiment of this application. Various modules included are used to perform steps S201 and S202, and steps S601 to S603. For ease of description, only parts related to this embodiment of this application are shown.

Refer to FIG. 14. The heart rhythm detection control apparatus provided in this embodiment of this application may be applied to the processor 180. The apparatus includes a detection module 1401 and a control module 1402.

The detection module 1401 is configured to detect motion data of a terminal in response to a heart rhythm detection instruction input by a user.

Optionally, the motion data includes a speed and/or acceleration of the terminal.

Optionally, the detection module 1401 is further configured to: if the motion data is greater than a motion data threshold, recognize ambient sound information of an environment in which the terminal is located; and if the ambient sound information includes preset vehicle characteristic information, display vehicle prompt information in the user interface, where the vehicle prompt information is used to prompt the user that the terminal is currently in a running vehicle.

The control module 1402 is configured to: if the motion data is greater than the motion data threshold, control the terminal to display first prompt information in the user interface, where the first prompt information is used to prompt the user that heart rhythm detection is suspended.

Optionally, the control module 1402 is further configured to control the terminal to display a confirm icon and an exit icon in the user interface, where the confirm icon is used to control the terminal to perform heart rhythm detection in response to a confirm operation input by the user; and the exit icon is used to control the terminal to exit the user interface in response to an exit operation input by the user.

Optionally, the control module 1402 is further configured to: when an automatic detection mode is enabled on the terminal, detect motion data of the terminal; and when detecting that the motion data is greater than the motion data threshold, suspend the automatic detection mode; or when detecting that the motion data is less than or equal to the motion data threshold, enable the automatic detection mode.

Optionally, the control module 1402 is further configured to: when detecting that the motion data is greater than the motion data threshold, display second prompt information in the user interface, where the second prompt information is used to prompt the user that the automatic detection mode is suspended.

Optionally, the control module 1402 is further configured to: when detecting that the motion data changes from being greater than the motion data threshold to being less than or equal to the motion data threshold, display third prompt information in the user interface, where the third prompt information is used to prompt the user that the automatic detection mode is enabled.

It should be noted that the information exchange, execution process, and other content between the foregoing modules are based on the same concept as the method embodiment of this application. For the specific functions and technical effects, refer to the method embodiment section for details, which are not described herein again.

It may be clearly understood by a person skilled in the art that, for the purpose of convenient and brief description, division of the foregoing functional modules is used as an example for illustration. In actual application, the foregoing functions can be allocated to different functional modules and implemented according to a requirement, that is, an inner structure of the apparatus is divided into different functional modules to implement all or some of the functions described above. The functional modules in the embodiments may be integrated into one processing unit, or each unit may be individually and physically present, or two or more units may be integrated into one unit. The integrated unit described above may be implemented in the form of hardware, or may be implemented in the form of software functional units. In addition, the specific names of the functional modules are only for the convenience of distinguishing from each other, and are not used to limit the protection scope of this application. For a specific working process of the modules in the foregoing system, refer to a corresponding process in the foregoing method embodiments. Details are not repeatedly described herein.

Corresponding to the heart rhythm detection control method provided in the foregoing embodiment, the processor of the terminal provided in this embodiment is further configured to perform steps S201 and S202, and steps S601 to S603 in the running process.

An embodiment further provides a computer-readable storage medium having a computer program stored thereon. When the computer program is executed by a processor, the steps of the foregoing method embodiments are implemented.

An embodiment of this application further provides a computer program product including instructions. The computer program product, when run on a computer or a processor, causes the computer or the processor to perform one or more steps of any one of the foregoing methods.

All or some of the foregoing embodiments may be implemented by using software, hardware, firmware, or any combination thereof. When software is used to implement the embodiments, all or a part of the embodiments may be implemented in a form of a computer program product. The computer program product includes one or more computer instructions. When the computer program instructions are loaded and executed on the computer, the procedure or functions according to embodiments of this application are all or partially generated. The computer may be a general-purpose computer, a dedicated computer, a computer network, or other programmable apparatuses. The computer instruction may be stored in a computer-readable storage medium, or may be transmitted by using the computer-readable storage medium. The computer instructions may be transmitted from a website, computer, server, or data center to another website, computer, server, or data center in a wired (for example, a coaxial cable, an optical fiber, or a digital subscriber line) or wireless (for example, infrared, radio, or microwave) manner. The computer-readable storage medium may be any usable medium accessible by the computer, or a data storage device, for example, a server or a data center, integrating one or more usable media.

A person of ordinary skill in the art may understand that all or some of the procedures of the methods in embodiments may be implemented by a computer program instructing related hardware. The program may be stored in the computer-readable storage medium. When the program is executed, the procedures of the methods in embodiments are performed. The storage medium includes any medium that can store program code, for example, a ROM or a random access memory RAM.

In conclusion, the foregoing descriptions are merely specific implementations of this application, but are not intended to limit the protection scope of this application. Any variation or replacement within the technical scope disclosed in this application shall fall within the protection scope of this application. Therefore, the protection scope of this application shall be subject to the protection scope of the claims.

What is claimed is:

1. A heart rhythm detection control method performed by a terminal, the method comprising:
   detecting motion data of the terminal in response to a heart rhythm detection instruction;
   when the motion data is greater than a motion data threshold, recognizing ambient sound information of an environment in which the terminal is located; and
   when the ambient sound information comprises vehicle characteristic information, displaying vehicle prompt information in a user interface of the terminal, wherein the vehicle prompt information is used to prompt that the terminal is currently in a running vehicle.

2. The heart rhythm detection control method according to claim 1, wherein a confirm icon and an exit icon are further displayed in the user interface, wherein the confirm icon is used to control the terminal to perform a heart rhythm detection in response to a confirm operation input by a user; and the exit icon is used to control the terminal to exit the user interface in response to an exit operation input by the user.

3. The heart rhythm detection control method according to claim 1, wherein when an automatic detection mode is enabled on the terminal, the method further comprises:
   detecting motion data of the terminal;
   when detecting that the motion data is greater than the motion data threshold, suspending the automatic detection mode; and
   when detecting that the motion data is less than or equal to the motion data threshold, enabling the automatic detection mode.

4. The heart rhythm detection control method according to claim 3, wherein when detecting that the motion data is greater than the motion data threshold, the method further comprises:
   displaying first prompt information in the user interface, wherein the first prompt information is used to prompt that the automatic detection mode is suspended.

5. The heart rhythm detection control method according to claim 3, wherein when detecting that the motion data changes from being greater than the motion data threshold to being less than or equal to the motion data threshold, the method further comprises:
   displaying second prompt information in the user interface, wherein the second prompt information is used to prompt that the automatic detection mode is enabled.

6. The heart rhythm detection control method according to claim 1, wherein the motion data comprises speed data and/or acceleration data, the speed data is based on Global Positioning System (GPS) data.

7. The heart rhythm detection control method according to claim 1, wherein the recognizing the ambient sound information of the environment in which the terminal is located comprises:
   collecting the ambient sound information;
   sending the ambient sound information to a server; and
   receiving a recognition result from the server.

8. The heart rhythm detection control method according to claim 1, further comprises:
   when the ambient sound information comprises preset vehicle characteristic information, removing interference from a collected Photo Plethysmo Graphy (PPG) signal to generate a first PPG signal; and
   detecting a heart rhythm based on the first PPG signal.

9. A terminal, comprising:
   a memory storing one or more computer program instructions; and
   one or more processors in communication with the memory, wherein the one or more processors execute the one or more computer program instructions to cause the terminal to perform the following steps:
   detecting motion data of the terminal in response to a heart rhythm detection instruction;
   recognizing ambient sound information of an environment in which the terminal is located when the motion data is greater than a motion data threshold; and
   displaying vehicle prompt information in a user interface of the terminal when the ambient sound information comprises vehicle characteristic information, wherein the vehicle prompt information is used to prompt that the terminal is currently in a running vehicle.

10. The terminal according to claim 9, wherein the one or more processors execute the one or more computer program instructions to cause the terminal to perform the following step:
   displaying a confirm icon and an exit icon in the user interface, wherein the confirm icon is used to control the terminal to perform heart rhythm detection in response to a confirm operation input by a user; and the exit icon is used to control the terminal to exit the user interface in response to an exit operation input by the user.

11. The terminal according to claim 9, wherein the one or more processors execute the one or more computer program instructions to cause the terminal to perform the following steps:
   when an automatic detection mode is enabled on the terminal, detecting the motion data of the terminal;
   when detecting that the motion data is greater than the motion data threshold, suspending the automatic detection mode; and
   when detecting that the motion data is less than or equal to the motion data threshold, enabling the automatic detection mode.

12. The terminal according to claim 11, wherein the one or more processors execute the one or more computer program instructions to cause the terminal to perform the following step:
   displaying first prompt information in the user interface, wherein the first prompt information is used to prompt that the automatic detection mode is suspended.

13. The terminal according to claim 11, wherein the one or more processors execute the one or more computer program instructions to cause the terminal to perform the following step:
   displaying second prompt information in the user interface, wherein the second prompt information is used to prompt that the automatic detection mode is enabled.

14. The terminal according to claim 9, wherein the motion data comprises speed data and/or acceleration data, the speed data being based on Global Positioning System (GPS) data.

15. The terminal according to claim 9, wherein the one or more processors execute the one or more computer program instructions to cause the terminal to perform the following steps:
   collecting the ambient sound information;
   sending the ambient sound information to a server; and
   receiving a recognition result from the server.

16. The terminal according to claim 9, wherein the one or more processors execute the one or more computer program instructions to cause the terminal to perform the following steps:
   when the ambient sound information comprises vehicle characteristic information, removing interference from a collected Photo Plethysmo Graphy (PPG) signal to generate a first PPG signal; and
   detecting a heart rhythm based on the first PPG signal.

17. A heart rhythm detection control method performed by a terminal, the method comprising:
   detecting motion data of the terminal in response to a heart rhythm detection instruction;
   when the motion data is greater than a motion data threshold, displaying first prompt information in a user interface of the terminal, wherein the first prompt information is used to prompt that heart rhythm detection is suspended; and
   when the motion data is lower than or equal to the motion data threshold, detecting the heart rhythm based on Photo Plethysmo Graphy (PPG) data.

18. The heart rhythm detection control method according to claim 17, wherein a confirm icon and an exit icon are further displayed in the user interface, wherein the confirm icon is used to control the terminal to perform a heart rhythm detection in response to a confirm operation input by a user; and the exit icon is used to control the terminal to exit the user interface in response to an exit operation input by the user.

19. The heart rhythm detection control method according to claim 17, wherein when detecting that the motion data is greater than the motion data threshold, the method further comprises:
   recognizing ambient sound information of an environment in which the terminal is located; and
   if the ambient sound information comprises vehicle characteristic information, displaying vehicle prompt information in the user interface, wherein the vehicle prompt information is used to prompt that the terminal is currently in a running vehicle.

20. The heart rhythm detection control method according to claim 19, wherein the recognizing ambient sound information of an environment in which the terminal is located comprises:
   collecting the ambient sound information;
   sending the ambient sound information to a server; and
   receiving a recognition result from the server.

* * * * *